(12) United States Patent
Hattori et al.

(10) Patent No.: US 8,420,668 B2
(45) Date of Patent: Apr. 16, 2013

(54) 1-(2H)-ISOQUINOLONE DERIVATIVE

(75) Inventors: Kazuo Hattori, Kamakura (JP);
Takehiro Okada, Kamakura (JP);
Osamu Kondoh, Kamakura (JP);
Toshiyuki Tsukaguchi, Kamakura (JP);
Masaki Shibata, Gotenba (JP); Satoshi Tanida, Gotenba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/131,422

(22) PCT Filed: Nov. 27, 2009

(86) PCT No.: PCT/JP2009/070004
§ 371 (c)(1),
(2), (4) Date: Aug. 9, 2011

(87) PCT Pub. No.: WO2010/061908
PCT Pub. Date: Jun. 3, 2010

(65) Prior Publication Data
US 2011/0282062 A1 Nov. 17, 2011

(30) Foreign Application Priority Data

Nov. 28, 2008 (JP) .................................. 2008-304548

(51) Int. Cl.
*C07D 413/04* (2006.01)
*A61K 31/47* (2006.01)

(52) U.S. Cl.
USPC .......................................... 514/309; 546/146

(58) Field of Classification Search ........................ None
See application file for complete search history.

(56) References Cited

U.S. PATENT DOCUMENTS

| | | | |
|---|---|---|---|
| 4,942,163 | A | 7/1990 | Behrens |
| 5,908,861 | A | 6/1999 | Kun |
| 6,303,629 | B1 | 10/2001 | Kun |
| 2007/0155798 | A1 | 7/2007 | Rhee et al. |
| 2007/0185160 | A1 | 8/2007 | Hattori et al. |
| 2008/0188467 | A1 | 8/2008 | Wong et al. |
| 2009/0030195 | A1 | 1/2009 | Hattori et al. |
| 2009/0192197 | A1 | 7/2009 | Rhee et al. |

FOREIGN PATENT DOCUMENTS

| | | | |
|---|---|---|---|
| CA | 2676984 A1 | 8/2008 | |
| WO | 9911624 A1 | 3/1990 | |
| WO | 9851307 A1 | 11/1998 | |
| WO | WO 9911624 A1 | 3/1999 | |
| WO | WO 9851307 A1 | 11/1999 | |
| WO | 2005058886 A1 | 6/2005 | |
| WO | 2005075431 A1 | 8/2005 | |
| WO | 2005075432 A1 | 8/2005 | |
| WO | WO 2005075431 A1 | 8/2005 | |
| WO | WO 2005075432 A1 | 8/2005 | |
| WO | 2006090743 A1 | 8/2006 | |
| WO | WO 2006090743 A1 | 8/2006 | |
| WO | 2008092231 A1 | 8/2008 | |
| WO | WO 2008092231 A1 | 8/2008 | |

OTHER PUBLICATIONS

Srivastva et al., "Bioreversible Phosphate Protective Groups: Synthesis and Stability of Model Acyloxymethyl Phosphates" Bioorganic Chemistry 12, 118-129 (1984).
European Search Report for EP 09829153.7 issued Jun. 27, 2012.
Barnwell, N. et al., "Selective Lipase-Catalysed Hydrolysis of a 1,2-Diester in the Development of a New Route to AZD2563 DSP", Organic Process Research & Development, 2006, vol. 10, No. 3, pp. 644-649.
Cheon, S.H. et al., "Structure-Activity Relationship Studies of Isoquinolinone Type Anticancer Agent", Archives of Pharmacal Research, 2001, vol. 24, No. 4, pp. 276-280.
Cho, W.J. et al., "Molecular Modeling of 3-Arylisoquinoline Antitumor Agents Active Against A-549. A Comparative Molecular Field Analysis Study", Bioorganic & Medicinal Chemistry, vol. 10, No. 9, 2002, pp. 2953-2961.
Cho, W.J. et al., "Synthesis and Antitumor Activity of 3-Arylisoquinoline Derivatives.", Archives Pharmacal Research, 1997, vol. 20, No. 3, pp. 264-268.
Cho, W.J. et al., "Synthesis and biological evaluation of 3-arylisoquinolines as antitumor agents", Bioorganic & Medicinal Chemistry Letters, 1998, vol. 8, No. 1, pp. 41-46.
Guastavino, J.F. et al., "One-Pot Synthesis of 3-Substituted Isoquinolin-1-(2H)-ones and Fused Isoquinolin-1-(2H)-ones by SRN1 Reactions in DMSO", European Journal of Organic Chemistry, 2006, No. 17, pp. 3898-3902, Sep. 2006.

(Continued)

*Primary Examiner* — Zinna Northington Davis

(74) *Attorney, Agent, or Firm* — Browdy and Neimark, PLLC

(57) ABSTRACT

The present invention provides a compound of the formula (I) or a pharmaceutically acceptable salt thereof:

[Formula 1]

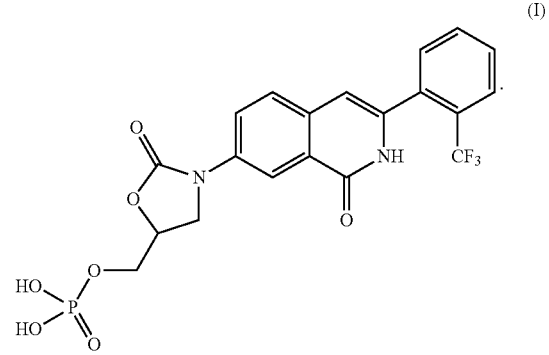

(I)

19 Claims, 2 Drawing Sheets

OTHER PUBLICATIONS

Le, T.N. et al., "A facile synthesis of benzo[c]phenanthridine alkaloids: oxynitidine and oxysanguinarine using lithiated toluamide-benzonitrile cycloaddition", Tetrahedron Letters, 2004, vol. 45, No. 13, pp. 2763-2766.

Le, T.N. et al., "A Versatile Total Synthesis of Benzo[c]phenanthridine and Protoberberine Alkaloids Using Lithiated Toluamide-Benzonitrile Cycloaddition", Journal Organic Chemistry, 2004, vol. 69, No. 8, pp. 2768-2772.

Poindexter, G.S., "Convenient Preparation of 3-Substituted 1(2H)-Isoquinolinones", Journal of Organic Chemistry, 1982, vol. 47, No. 19, pp. 3787-3788.

Rose, A. et al., "Oxygen heterocycles. Part XIII. From 3-Arylisocoumarins to 3-Arylisoquinolines and 4-Aryl-5H-2,3-benzodiazepines", Journal of the Chemical Society C, 1968, pp. 2205-2208.

Cimpean et al., Substrate-specifying determinants of the nucleotide pyrophosphatases/phosphodiesterases NPP1 and NPP2, Biochem. J., 381:71-77 (2004).

1-(2H)-ISOQUINOLONE DERIVATIVE

This application is a 371 of PCT/JP2009/070004 filed Nov. 27, 2009.

TECHNICAL FIELD

The present invention relates to a novel 1-(2H)-isoquinolone derivative and a pharmaceutical agent comprising the same as an active ingredient, in particular, an antitumor agent useful as a therapeutic agent against a disease such as solid cancer.

BACKGROUND ART

Regarding a method for synthesizing a 1-(2H)-isoquinolone derivative having a substituent at position 3, several reports have already been made. For example, in 1968, Rose et al. reported a method for synthesizing a 1-(2H)-isoquinolone derivative by reacting a 3-arylisocoumarin derivative with ammonia (see Non-patent Document 1). Further, in 1982, Poindexter reported a method for synthesizing a 1-(2H)-isoquinolone derivative by reacting N,2-dimethylbenzamide with a nitrile derivative (see Non-patent Document 2).

The pharmacological activity of these isoquinolone derivatives has also been reported. Researchers of Octamer, Inc. reported an isoquinolone derivative having anti-inflammatory action (see Patent Document 1). Researchers of Guilford, Inc. reported that 3-phenyl-1-(2H)-isoquinolone had inhibitory activity against poly(ADP-ribose) polymerase, and also reported the use of 3-phenyl-1-(2H)-isoquinolone as a radiosensitizer (see Patent Document 3). Further, it is reported that 3-phenyl-1-(2H)-isoquinolone is effective for prevention or treatment of cardiovascular disease (see Patent Documents 4 and 5).

In 1989, researchers of Du Pont reported that a 3-(1-naphthyl)-1-(2H)-isoquinolone derivative had anticancer activity (see Patent Document 2). Furthermore, it is reported that a 1-(2H)-isoquinolone derivative and a prodrug thereof have anticancer activity (see Patent Documents 6 to 8). Following the above reports, Won-Jea Cho et al. reported a 3-arylisoquinolone derivative having anticancer action (see Non-patent Documents 3 to 8).

Further, Guastavino, Javier F, et al. reported an efficient method for the synthesis of an isoquinolone derivative (see Non-patent Document 9).

CITATION LIST

Patent Documents

Patent Document 1: International publication No. WO98/51307
Patent Document 2: U.S. Pat. No. 4,942,163
Patent Document 3: International publication No. WO99/11624
Patent Document 4: International publication No. WO2008/092231
Patent Document 5: United States patent application publication No. 2008/0188467
Patent Document 6: International publication No. WO2005/075431
Patent Document 7: International publication No. WO2005/075432
Patent Document 8: International publication No. WO2006/090743

Non-Patent Documents

Non-patent Document 1: J. Chem. Soc.(C), pp. 2205-2208 (1968)
Non-patent Document 2: J. Org. Chem., Vol. 47, pp. 3787-3788 (1982)
Non-patent Document 3: Arch. Pharm. Res., Vol. 20, pp. 264-268 (1997)
Non-patent Document 4: Bioorg. Med. Chem. Lett., Vol. 8, pp. 41-46 (1998)
Non-patent Document 5: Arch. Pharm. Res., Vol. 24, pp. 276-280 (2001)
Non-patent Document 6: Bioorg. Med. Chem., Vol. 10, pp. 2953-2961 (2002)
Non-patent Document 7: Tetrahedron Lett., Vol. 45, pp. 2763-2766 (2004)
Non-patent Document 8: J. Org. Chem., Vol. 69, pp. 2768-2772 (2004)
Non-patent Document 9: European Journal of Organic Chemistry, Vol. 17, pp. 3898-3902 (2006)

SUMMARY OF INVENTION

Technical Problem

Although many reports have been made as described above, there has not been any isoquinolone derivative or a prodrug thereof available as a practical compound for use as an anticancer agent. Thus, there have been demands for a compound having high anticancer activity and also having preferred properties as a pharmaceutical agent.

An object of the present invention is to provide a compound which has high antitumor activity and is useful as a pharmaceutical agent effective for treatment and prevention of a proliferative disease such as cancer, in particular, a compound having preferred properties as a pharmaceutical agent, a crystal thereof, a method for the production thereof, an intermediate compound useful for the production, and a pharmaceutical composition comprising such a compound.

Solution to Problem

The present inventors conducted intensive and extensive studies in an attempt to provide a novel compound effective for treatment or prevention of a proliferative disease such as cancer. Consequently, they found that a compound of the present invention had excellent antitumor activity, had excellent water solubility which made the compound suitable for administration by intravenous injection, was excellent in terms of the rate of conversion into an active substance, and had preferred properties as a pharmaceutical product in terms of safety and the like. These findings led to the completion of the present invention.

Specifically, in one aspect of the present invention, a compound, or pharmaceutically acceptable salts thereof, or crystals thereof are provided as follows:

(1) A compound of the formula (I):

[Formula 1]

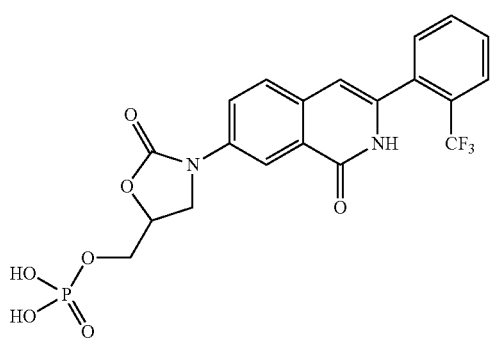

(I)

or a pharmaceutically acceptable salt thereof;

(2) A compound of the formula (I):

[Formula 2]

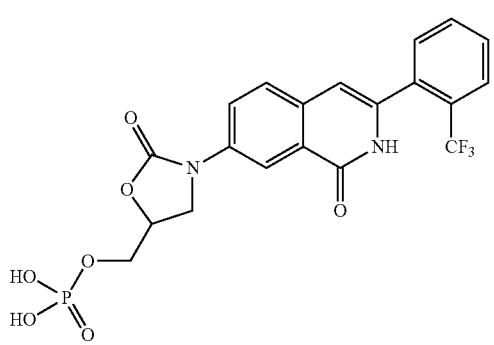

(I)

or sodium or potassium salt thereof;

(3) A compound of the formula (II):

[Formula 3]

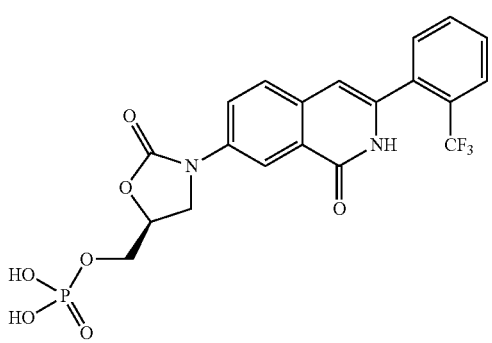

(II)

or a disodium or monopotassium salt thereof;

(4) A crystal of a compound of the formula (II):

[Formula 4]

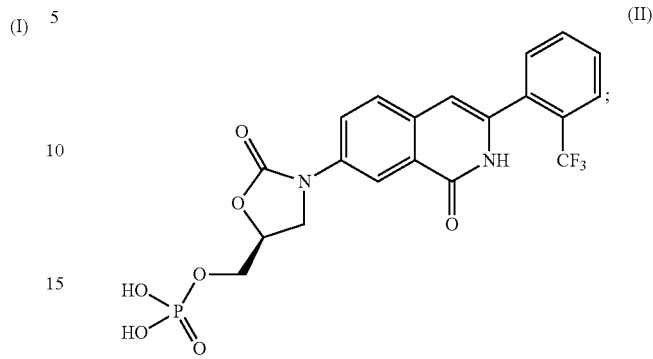

(II)

(5) The crystal of the compound of the formula (II) according to (4), wherein the crystal has peaks at diffraction angles (2θ) of around 3.9°, 9.1°, 10.7°, 13.4°, 18.0°, 21.6°, 23.8°, and 24.8° in powder X-ray diffraction;

(6) The crystal of the compound of the formula (II) according to (4), wherein the crystal has peaks at diffraction angles (2θ) of around 3.3°, 3.9°, 9.1°, 10.7°, 11.9°, 13.4°, 14.2°, 15.2°, 16.5°, 17.4°, 18.0°, 19.2°, 19.9°, 20.6°, 21.6°, 22.1°, 22.6°, 23.8°, 24.3°, 24.8°, and 25.6° in powder X-ray diffraction;

(7) A crystal of a monopotassium salt of a compound of the formula (II):

[Formula 5]

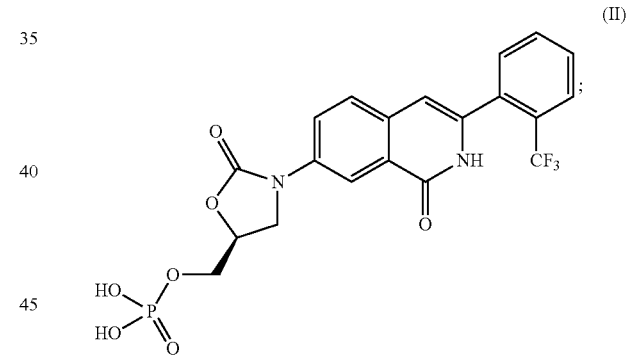

(II)

(8) The crystal of the monopotassium salt of the compound of the formula (II) according to (7), wherein the crystal has peaks at diffraction angles (2θ) of around 4.5°, 9.2°, 12.2°, 16.6°, 18.7°, 21.2°, 22.4°, and 26.2° in powder X-ray diffraction; and (9) The crystal of the monopotassium salt of the compound of the formula (II), wherein the crystal has peaks at diffraction angles (2θ) of around 3.6°, 4.5°, 9.2°, 10.9°, 12.2°, 13.7°, 15.3°, 16.6°, 18.0°, 18.7°, 19.3°, 21.2°, 22.4°, 24.3°, 26.2°, and 28.8° in powder X-ray diffraction.

In another aspect, the present invention provides the following pharmaceutical compositions:

(10) A pharmaceutical composition comprising the compound of any one of (1) to (9), or a pharmaceutically acceptable salt or a crystal thereof as an active ingredient;

(11) The pharmaceutical composition of (10) for use in a treatment or prevention of a malignant tumor;

(12) The pharmaceutical composition of (11), wherein the malignant tumor is solid cancer; and

(13) The pharmaceutical composition of any one of (10) to (12), wherein a dosage form of the composition is an injection.

Advantageous Effect of Invention

The present invention provides a 1-(2H)-isoquinolone derivative having excellent antitumor action and preferred characteristics as a pharmaceutical agent in terms of disposition and safety. The present invention also provides a compound or a pharmaceutically acceptable salt thereof or a crystal thereof, and a pharmaceutical composition comprising such a compound useful in treating and preventing a proliferative disease such as cancer.

DESCRIPTION OF EMBODIMENT

Figure 1:
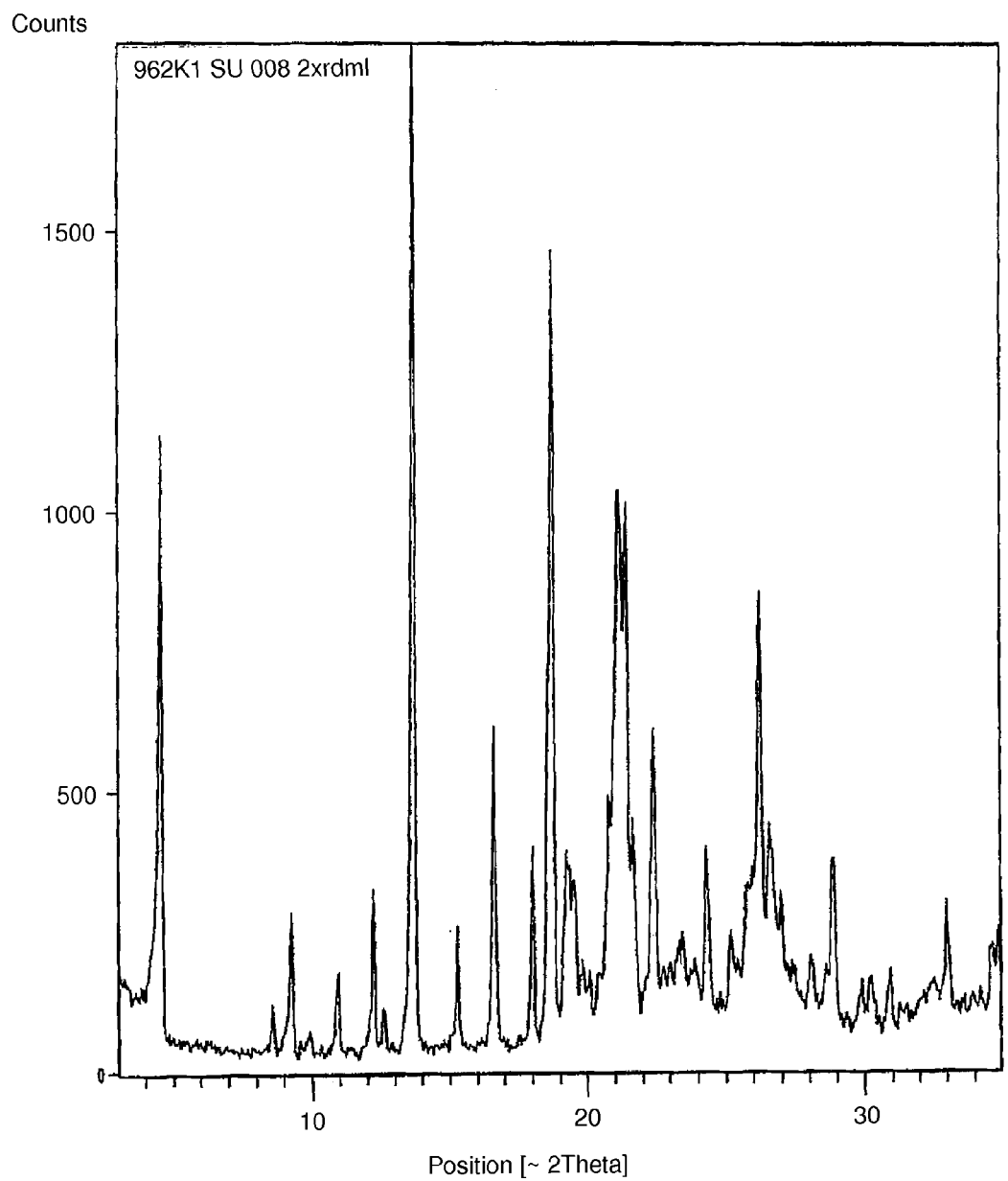
FIG. 1 is one example of the results of powder X-ray diffraction measurement of a crystal of mono-{(S)-2-oxo-3-[1-oxo-3-(2-trifluoromethyl-phenyl)-1,2-dihydro-isoquinoline-7-yl]-oxazolidine-5-ylmethyl}-monopotassium phosphate prepared in Example 3.

The present invention includes a salt of the compound represented by the formula (I). This salt can be produced by contacting the compound of the formula (I) with a base which can be used in the production of a pharmaceutical product. Examples of such a salt include alkali metal salts such as sodium salts and potassium salts; alkaline earth metal salts such as magnesium salts and calcium salts; ammonium salts such as ammonium salts, alkylammonium salts, dialkylammonium salts, trialkylammonium salts, and tetraalkylammonium salts; amino acid salts such as lysine and arginine, etc.

In one embodiment of the present invention, the compound of the above formula (I) or (II) or a pharmaceutically acceptable salt thereof is absorbed as a water soluble prodrug, and metabolized to 7-(5-hydroxymethyl-2-oxooxazolidine-3-yl)-3-(2-trifluoromethylphenyl)-2H-isoquinolin-1-one, which serves as an active substance. The active substance is disclosed in International publication No. WO2006/090743 as example compounds (1-13: 7-((S)-5-hydroxymethyl-2-oxooxazolidine-3-yl)-3-(2-trifluoromethylphenyl)-2H-isoquinolin-1-one) or (1-14:7-((R)-5-hydroxymethyl-2-oxooxazolidine-3-yl)-3-(2-trifluoromethylphenyl)-2H-isoquinolin-1-one).

The compound of the present invention and pharmaceutically acceptable salts thereof can exist in several forms of tautomers and mixtures thereof. In general, a tautomer in a solution is present as mixtures of tautomers, and one tautomer is dominant in a case of a solid form. As used herein, a single tautomer of a particular compound is intended to mean any of all tautomers corresponding to the compound.

Crystals of the compound of the present invention can be obtained by, for example, preparing a solution of the compound and conducting a procedure such as cooling, pH adjustment, removal of a solvent by lyophilization or the like, or addition of an anti-solvent. Crystals of the compound of the above formula (II) can be obtained as hydrates (particularly monohydrate). These crystals can be prepared by, for example, cooling a high concentration solution of the compound of the above formula (II) in a highly polar solvent (water, methanol, ethanol, acetone, etc.), or by adjusting the pH. Examples of a solvent that can be used as an anti-solvent include heptane, t-butyl methyl ether, etc. There are at least two forms (hydrate 1 and hydrate 2). Further, there are cases where the compound of the present invention forms solvates other than hydrates, and such solvates are also included in the technical scope of the present invention.

The compound of the above formula (I) or (II) can be converted into salts, hydrates, or solvates of the compound by a commonly-used method. On the other hand, the compound of the above formula (I) or (II) can be prepared from salts, hydrates, or solvates of the compound by a commonly-used method.

The compound of the present invention or pharmaceutically acceptable salts thereof have excellent antitumor action, are excellent in solubility in water, and are useful in preventing or treating (particularly in treating) proliferative disease including cancer. Further, the compound of the present invention or pharmaceutically acceptable salts thereof are useful in preventing or treating (particularly in treating) various cancers, such as breast cancer, colon cancer, ovarian cancer, lung cancer, pancreatic cancer, liver cancer, uterine cancer, brain tumor, prostatic cancer, blood cancer (e.g., acute leukemia, malignant lymphoma, etc.), bladder cancer, esophageal cancer, skin cancer, testicular cancer, thyroid cancer, and gastric cancer, and in particular, solid cancers such as breast cancer, colon cancer, ovarian cancer, lung cancer, pancreatic cancer, liver cancer, uterine cancer, brain tumor, prostatic cancer, and gastric cancer. Furthermore, the compound of the present invention has characteristics such as fewer effects (e.g., enzyme inhibition, etc.) on a drug metabolizing enzyme such as CYP3A4; the compound of the present invention has preferred effects as a pharmaceutical agent in terms of safety.

In a case of using the pharmaceutical composition of the present invention as an agent for treating or preventing a proliferative disease such as cancer, examples of an administration method include oral, rectal, parenteral (intravenous, intramuscular, subcutaneous), intracisternal, intravaginal, intraperitoneal, intravesical, and topical (administration of drop, powder, ointment, gel, or cream) administrations, inhalation (intraoral or nasal spray), etc. Preferred is parenteral administration, particularly intravenous administration. Examples of a dosage form of the pharmaceutical composition include a tablet, a capsule, a granule, a powder, a pill, an aqueous or nonaqueous oral solution or suspension, a parenteral solution which is filled in a container suitable for dividing the solution into individual dosages, etc. Further, the form of administration can also be adapted to various administration methods including controlled release preparations such as those used in subcutaneous transplantation.

The above formulations are produced by a well-known method using an additive(s) such as an excipient, a lubricant (coating agent), a binder, a disintegrator, stabilizer, a flavoring agent, a diluent, etc.

Examples of an excipient include starches such as starch, potato starch, and corn starch, lactose, crystalline cellulose, calcium hydrogen phosphate, etc. Examples of a coating agent include ethyl cellulose, Hydroxypropyl cellulose, hydroxypropylmethyl cellulose, shellac, talc, carnauba wax, paraffin, etc.

Examples of a binder include polyvinyl pyrrolidone, macrogol, and the same compounds as those described above as examples of an excipient.

Examples of a disintegrator include the same compounds as those described above as examples of an excipient, and chemically modified starches and celluloses such as croscarmellose sodium, carboxymethyl starch sodium, crosslinked polyvinyl pyrrolidine, etc.

Examples of a stabilizer include p-hydroxybenzoic esters such as methylparaben and propylparaben; alcohols such as chlorobutanol, benzyl alcohol, and phenylethyl alcohol; benzalkonium chloride; phenols such as phenol and cresol; thimerosal; dehydroacetic acid; and sorbic acid.

Examples of a flavoring agent include commonly-used sweeteners, acidulants, aromatics, etc.

Further, examples of a solvent that can be used in production of a liquid agent include ethanol, phenol, chlorocresol, purified water, distilled water, etc.

Examples of a surfactant or emulsifier include polysorbate 80, polyoxyl 40 stearate, lauromacrogol, etc.

The dosage of compounds of the above formulas (I) and (II) or a pharmaceutically acceptable salt thereof varies depending on a symptom, age, body weight, relative physical condition, the use of other drugs, administration method, etc. For example, in a case of administering an active ingredient (compound of the present invention represented by the formula (I)) as an oral agent to a patient (warm-blooded animal, particularly human), the dosage may be in the range of preferably 0.01 to 5000 mg, more preferably 0.1 to 500 mg, per kilogram of body weight per day. In a case of administering as a parenteral agent, the dosage may be in the range of preferably 0.01 to 5000 mg, more preferably 0.1 to 500 mg, per kilogram of body weight per day. It is desirable to determine the dosage as appropriate to the symptom.

EXAMPLES

The present invention is described in detail by the following Examples. However, it is understood that the scope of the present invention is not limited by the Examples. Note that NMR analysis was conducted with a JNM-EX270 (270 MHz) manufactured by JEOL, JNMGSX400 (400 MHz) manufactured by JEOL, JNM-A500 (500 MHz) manufactured by JEOL, or NMR (300 MHz) manufactured by Bruker. NMR data was indicated in ppm (parts per million). The deuterium lock signal from a deuterated solvent was referred to. The optical rotation was determined with a DIP-1000 manufactured by JASCO (Nihon Bunko). The powder X-ray diffraction was measured with a PW-3050 (Philips) The vapor adsorption/desorption isotherm was measured with a dynamic vapor adsorption isothermal instrument DVS-1 (Surface Measurement Systems). The melting point was measured with a thermal analyzer TG/DTA6200 (Seiko). The mass spectrum data was obtained with a JMS-DX303 or JMS-SX/SX102A manufactured by JEOL, Quttromicro manufactured by Micromass, or GCmate manufactured by JEOL. As a mass spectrometer equipped with a high-performance liquid chromatography, a micromass (ZMD manufactured by Micromass) equipped with a 996-600E gradient high-performance liquid chromatography manufactured by Waters, a micromass (ZQ manufactured by Micromass) equipped with a 2525 or 3100 gradient high-performance liquid chromatography manufactured by Waters was used.

Specific measurement conditions are specified below.
Conditions of High-Performance Liquid Chromatography
Column: Sun Fire C18 (ODS, 5 μm, 4.6 mm I.D.×50 mm, manufactured by Waters);
Mobile phase: (A) Water containing 0.05% trifluoroacetic acid and (B) acetonitrile containing 0.05% trifluoroacetic acid;

Elution method: Stepwise solvent gradient elution from 10% B to 95% B (3.5 min), from 95% B to 10% B (1 min), and then retaining at 10% B (0.5 min);
Flow rate: 4.0 mL/min
Conditions of Measurement of Powder X-Ray Diffraction:
Anticathode: Cu;
Tube voltage: 50 kV;
Tube current: 40 mA;
Scan speed: 0.017°/s;
Step size: 0.05°;
Divergence slit: 0.25°;
Scattering slit: 0.25°;
Receiving slit: 0.20 mm
Scan range: 3 to 35°.
Conditions of Measurement of Melting Point:
Temperature: 30° C. to 350° C.;
Heating rate: 10° C./min.;
Gas flow rate: Nitrogen gas, 300 mL/min An organic synthesis reaction was carried out using a commercially-available reagent which was not further purified. The room temperature refers to a range of about 20 to about 25° C. All reactions requiring anhydrous conditions were carried out under a nitrogen atmosphere. Unless otherwise specified, concentration or removal of solvent under reduced pressure was carried out using a rotary evaporator.

In the preparation of the compound, as necessary, a functional group(s) was protected with a protective group(s), and the protective group(s) was removed after a protector for a target molecule was prepared. Procedures for selecting and removing such a protective group(s) were carried out by, for example, a technique described in Greene and Wuts, "Protective Group in Organic Synthesis," second edition, John Wiley & Sons, 1991.

Example 1

Mono-{(S)-2-oxo-3-[1-oxo-3-(2-trifluoromethyl-phenyl)-1,2-dihydro-isoquinolin-7-yl]-oxazolidin-5-ylmethyl}-phosphoric acid

[Formula 6]

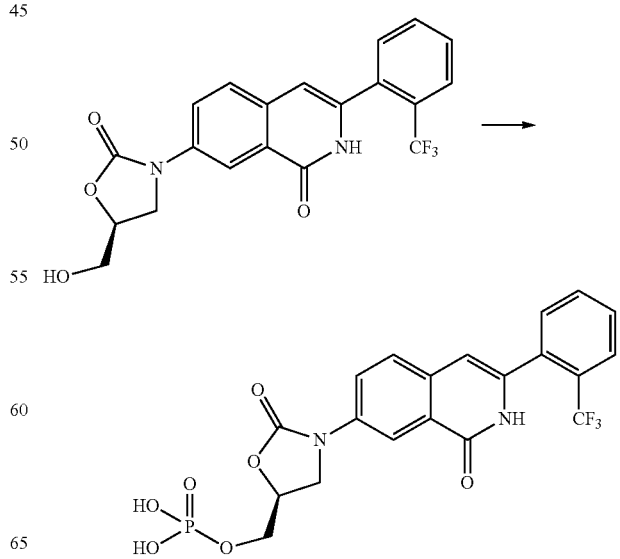

To an acetonitrile solution (1.5 mL) of phosphorus oxychloride (1.5 g, 9.79 mmol), water (0.112 mL, 6.23 mmol) and 1-butylimidazole (1.4 mL, 10.7 mmol) were added on ice, and the mixture was stirred for 5 minutes. Thereafter, a solution of 7-((S)-5-hydroxymethyl-2-oxooxazolidin-3-yl)-3-(2-trifluoromethylphenyl)-2H-isoquinolin-1-one (prepared by the method described in WO2006/090743, 900 mg, 2.23 mmol) in acetonitrile (3 mL) was added on ice, and then the mixture was immediately back to room temperature and stirred at room temperature for 3 hours. To the resulting mixture, ice (5 g) was added and stirred for 30 minutes. Then, 1N hydrochloric acid was added, followed by extraction with ethyl acetate. The combined organic layers were dried with anhydrous magnesium sulfate, and then the solvent was removed under reduced pressure. The resulting residue was purified by preparative liquid chromatography (TSK-GEL manufactured by TOSOH, ODS-80TS55×300 mm: $H_2O$/$CH_3CN$ (0.05% TFA)=43:27), whereby the title compound was obtained as a white powder substance (612 mg, 57%).

$^1$H-NMR (DMSO-$d_6$) δ: 3.97 (1H, dd, J=8.9, 6.2 Hz), 4.06 (1H, ddd, J=12.0, 5.0 Hz, $J_{HP}$=6.9 Hz), 4.13 (1H, ddd, J=12.0, 3.0 Hz, $J_{HP}$=5.4 Hz), 4.26 (1H, t, J=8.9 Hz), 4.94 (1H, m), 6.48 (1H, s), 7.62 (1H, d, J=7.6 Hz), 7.70 (1H, t, J=7.6 Hz), 7.73 (1H, d, J=8.8 Hz), 7.77 (1H, t, J=7.6 Hz), 7.86 (1H, d, J=7.6 Hz), 8.08 (1H, dd, J=8.8, 2.4 Hz), 8.21 (1H, d, J=2.4 Hz), 11.61 (1H, s).

ESI (LC-MS positive mode) m/z 485 (M+H)

Example 2

Mono-{(S)-2-oxo-3-[1-oxo-3-(2-trifluoromethyl-phenyl)-1,2-dihydro-isoquinolin-7-yl]-oxazolidin-5-ylmethyl}-disodium phosphate

[Formula 7]

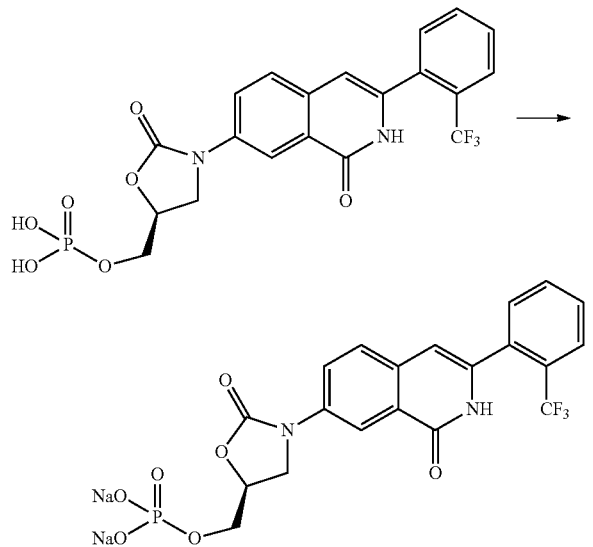

To a suspension of mono-{(S)-2-oxo-3-[1-oxo-3-(2-trifluoromethyl-phenyl)-1,2-dihydro-isoquinolin-7-yl]-oxazolidin-5-ylmethyl}-phosphoric acid (Example 1, 1.1 g, 2.21 mmol) in water (5 mL), 1N NaOH (4.3 mL, 4.3 mmol) was added at room temperature, and the mixture was stirred for 1 hour to give a solution. This solution was lyophilized to give the title compound as a white powder (1.11 g, 93%).

$^1$H-NMR ($D_2O$) δ: 3.97-4.23 (3H, m), 4.29-4.39 (1H, m), 4.95-5.14 (1H, m), 6.82 (1H, s), 7.61 (1H, d, J=8.1 Hz), 7.67-7.83 (3H, m), 7.91 (1H, d, J=8.1 Hz), 8.07 (1H, dd, J=2.5, 8.1 Hz), 8.27 (1H, d, J=2.5 Hz).

ESI (LC-MS positive mode) m/z 485 (M+H)

$[α]_D$: +53.0 (C=1.05, $H_2O$)

Example 3

Mono-{(S)-2-oxo-3-[1-oxo-3-(2-trifluoromethyl-phenyl)-1,2-dihydro-isoquinolin-7-yl]-oxazolidin-5-ylmethyl}-monopotassium phosphate

[Formula 8]

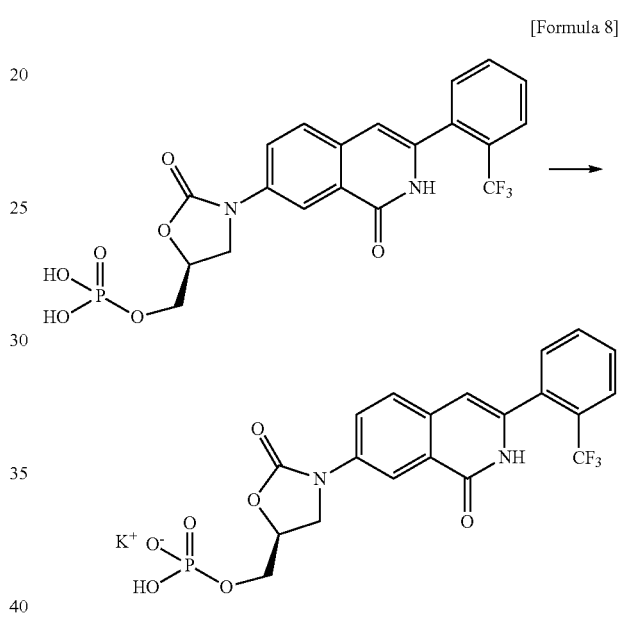

To mono-{(S)-2-oxo-3-[1-oxo-3-(2-trifluoromethyl-phenyl)-1,2-dihydro-isoquinolin-7-yl]-oxazolidin-5-ylmethyl}-phosphoric acid (Example 1, 253.6 mg), ethanol (1.25 mL) was added and dissolved at 60° C. An aqueous solution of 1N potassium hydroxide (0.524 mL) was added, and seed crystals of title compound were added. Thereafter, the mixture was cooled to room temperature and then shaken. After precipitation of a solid was confirmed, the resulting precipitate was filtered and then dried under reduced pressure to give the title crystals (201.7 mg).

$^1$H-NMR ($D_2O$) δ: 4.02-4.13 (3H, m), 4.14-4.23 (2H, m), 4.26 (1H, t, J=9.3 Hz), 4.97-5.06 (1H, m), 6.60 (1H, s), 7.48 (1H, d, J=6.8 Hz), 7.57 (1H, d, J=8.8 Hz), 7.60-7.71 (2H, m), 7.82 (1H, d, J=6.8 Hz), 7.91 (1H, dd, J=8.8, 2.3 Hz), 8.08 (1H, d, J=2.3 Hz).

ESI (LC-MS positive mode) m/z 485 (M+H).

FABMS (positive mode) m/z 485 (M+H), 523 (M−H+K+H), 561 (M−2H+2K+H).

Melting point: An endothermic peak was observed at around 270° C.

Powder X-ray diffraction: Peaks were observed at diffraction angles (2θ) of around 3.6°, 4.5°, 9.2°, 10.9°, 12.2°, 13.7°, 15.3°, 16.6°, 18.0°, 18.7°, 19.3°, 21.2°, 22.4°, 24.3°, 26.2°, and 28.8°. The chart is shown in FIG. 1.

Reference Example 1

Seed crystals used in Example 3 were obtained by the following procedure.

To mono-{(S)-2-oxo-3-[1-oxo-3-(2-trifluoromethyl-phenyl)-1,2-dihydro-isoquinolin-7-yl]-oxazolidin-5-ylmethyl}-phosphoric acid (10.5 mg), ethanol (105 μL) was added and dissolved at 60° C. Thereafter, 1N potassium hydroxide solution (21.7 μL) was added, and the mixture was cooled to room temperature. Then, the mixture was heated to 40° C. and stirred while evaporating ethanol to give a precipitate. The resulting precipitate was filtered and then dried under reduced pressure to give a powder.

Example 4

Crystal of mono-{(S)-2-oxo-3-[1-oxo-3-(2-trifluoromethyl-phenyl)-1,2-dihydro-isoquinolin-7-yl]-oxazolidin-5-ylmethyl}-phosphoric acid (hydrate 2)

To mono-{(S)-2-oxo-3-[1-oxo-3-(2-trifluoromethyl-phenyl)-1,2-dihydro-isoquinolin-7-yl]-oxazolidin-5-ylmethyl}-phosphoric acid (51.9 mg), an aqueous solution of 0.1N sodium hydroxide (1.572 mL) was added and dissolved at room temperature. Then, ethanol (0.472 mL) was added, and 1N hydrochloric acid (0.157 mL) was added with stirring. To this solution, seed crystals of the title compound were added and then shaken. The resulting precipitate was recovered by filtration and then dried under reduced pressure to give the title crystal (hydrate 2, 37.4 mg).

$^1$H-NMR (DMSO-$d_6$) δ: 3.97 (1H, dd, J=8.9, 6.2 Hz), 4.06 (1H, ddd, J=12.0, 5.0 Hz, JHP=6.9 Hz), 4.13 (1H, ddd, J=12.0, 3.0 Hz, JHP=5.4 Hz), 4.26 (1H, t, J=8.9 Hz), 4.94 (1H, m), 6.48 (1H, s), 7.62 (1H, d, J=7.6 Hz), 7.70 (1H, t, J=7.6 Hz), 7.73 (1H, d, J=8.8 Hz), 7.77 (1H, t, J=7.6 Hz), 7.86 (1H, d, J=7.6 Hz), 8.08 (1H, dd, J=8.8, 2.4 Hz), 8.21 (1H, d, J=2.4 Hz), 11.61 (1H, s).

ESI (LC-MS positive mode) m/z 485 (M+H).

Melting point: An endothermic peak was observed at around 161° C.

Figure 2:
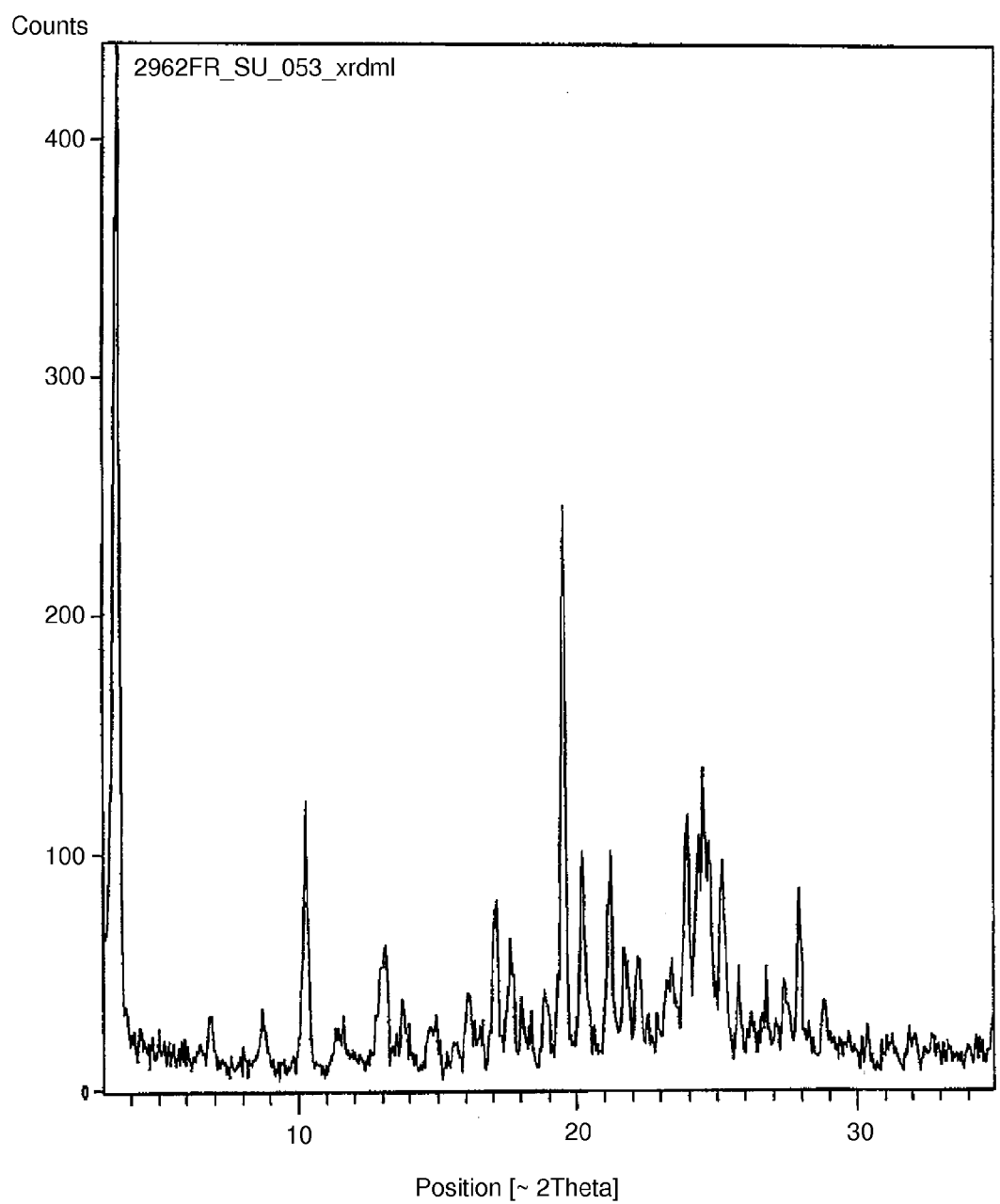
FIG. 2 is one example of the results of powder X-ray diffraction measurement of a crystal (hydrate crystal type 2) of mono-{(S)-2-oxo-3-[1-oxo-3-(2-trifluoromethyl-phenyl)-1,2-dihydro-isoquinoline-7-yl]-oxazolidine-5-ylmethyl}-phosphoric acid prepared in Example 4.

Powder X-ray diffraction: Peaks were observed at diffraction angles (2θ) of around 3.3°, 3.9°, 9.1°, 10.7°, 11.9°, 13.4°, 14.2°, 15.2°, 16.5°, 17.4°, 18.0°, 19.2°, 19.9°, 20.6°, 21.6°, 22.1°, 22.6°, 23.8°, 24.3°, 24.8°, and 25.6°. The chart is shown in FIG. 2.

Reference Example 2

Seed crystals used in Example 4 were obtained by the following procedure.

To mono-{(S)-2-oxo-3-[1-oxo-3-(2-trifluoromethyl-phenyl)-1,2-dihydro-isoquinolin-7-yl]-oxazolidin-5-ylmethyl}-phosphoric acid (9.1 mg), water (91 μL) was added and dissolved at 60° C. Thereafter, the mixture was cooled to room temperature to give a precipitate. The resulting precipitate was filtered and then dried under reduced pressure to give a powder.

Example 5

Crystal of mono-{(S)-2-oxo-3-[1-oxo-3-(2-trifluoromethyl-phenyl)-1,2-dihydro-isoquinolin-7-yl]-oxazolidin-5-ylmethyl}-phosphoric acid (hydrate crystal type 1)

To mono-{(S)-2-oxo-3-[1-oxo-3-(2-trifluoromethyl-phenyl)-1,2-dihydro-isoquinolin-7-yl]-oxazolidin-5-ylmethyl}-phosphoric acid (250 mg), ethanol (1.25 mL) was added and dissolved at 80° C. Then, the mixture was cooled to room temperature, and thereafter seed crystals of the title compound were added and then shaken. After precipitation of a solid was confirmed, the resulting precipitate was filtered and then dried under reduced pressure to give the title crystal (hydrate 1, 213.2 mg).

Melting point: An endothermic peak was observed at around 163° C.

Reference Example 3

Seed crystals used in Example 5 were obtained by the following procedure.

To mono-{(S)-2-oxo-3-[1-oxo-3-(2-trifluoromethyl-phenyl)-1,2-dihydro-isoquinolin-7-yl]-oxazolidin-5-ylmethyl}-phosphoric acid (82.3 mg), dimethylsulfoxide (823 μL) was added and dissolved. The prepared solution (30 μL) was lyophilized. To the resulting powder, ethanol (15 μL) and heptane (15 μL) were added and stirred at room temperature to give a precipitate. The resulting precipitate was filtered and then dried under reduced pressure to give a powder.

Example 6

Mono-{(R)-2-oxo-3-[1-oxo-3-(2-trifluoromethyl-phenyl)-1,2-dihydro-isoquinolin-7-yl]-oxazolidin-5-ylmethyl}-phosphoric acid

[Formula 9]

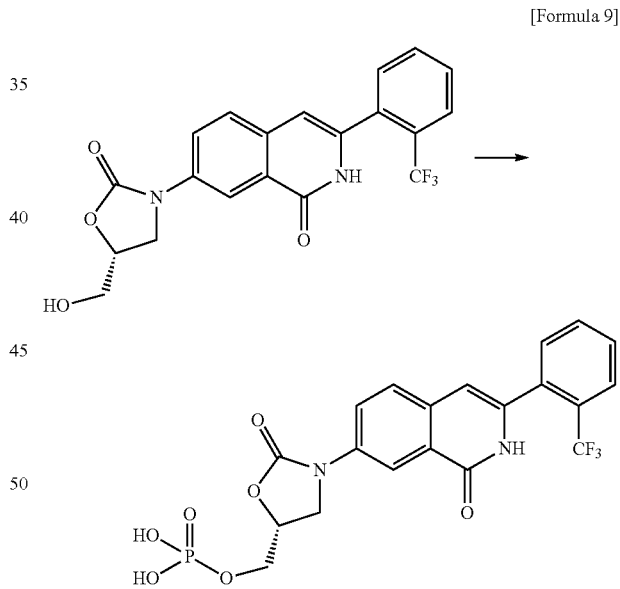

The title compound was obtained by a method similar to that described in Example 1 using 7-((R)-5-hydroxymethyl-2-oxooxazolidin-3-yl)-3-(2-trifluoromethylphenyl)-2H-isoquinolin-1-one as a starting material.

$^1$H-NMR (DMSO-$d_6$) δ: 3.97 (1H, dd, J=8.9, 6.2 Hz), 4.06 (1H, ddd, J=12.0, 5.0 Hz, JHP=6.9 Hz), 4.13 (1H, ddd, J=12.0, 3.0 Hz, JHP=5.4 Hz), 4.26 (1H, t, J=8.9 Hz), 4.94 (1H, m), 6.48 (1H, s), 7.62 (1H, d, J=7.6 Hz), 7.70 (1H, t, J=7.6 Hz), 7.73 (1H, d, J=8.8 Hz), 7.77 (1H, t, J=7.6 Hz), 7.86 (1H, d, J=7.6 Hz), 8.08 (1H, dd, J=8.8, 2.4 Hz), 8.21 (1H, d, J=2.4 Hz), 11.61 (1H, s).

ESI (LC-MS positive mode) m/z 485 (M+H)

Example 7

Mono-{(R)-2-oxo-3-[1-oxo-3-(2-trifluoromethyl-phenyl)-1,2-dihydro-isoquinolin-7-yl]-oxazolidin-5-ylmethyl}-disodium phosphate

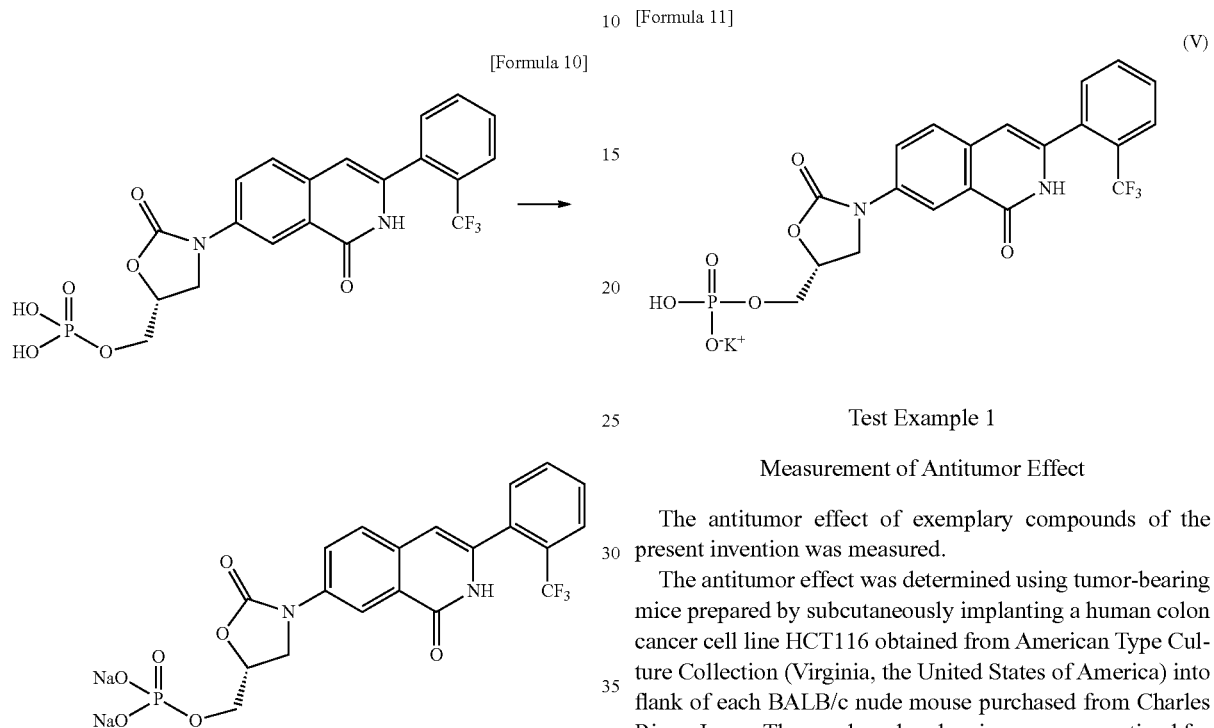

[Formula 10]

[Formula 11]

The title compound was obtained by a method similar to that described in Example 2 using mono-{(R)-2-oxo-3-[1-oxo-3-(2-trifluoromethyl-phenyl)-1,2-dihydro-isoquinolin-7-yl]-oxazolidin-5-ylmethyl}-phosphoric acid.

$^1$H-NMR (D$_2$O) δ: 3.97-4.23 (3H, m), 4.29-4.39 (1H, m), 4.95-5.14 (1H, m), 6.82 (1H, s), 7.61 (1H, d, J=8.1 Hz), 7.67-7.83 (3H, m), 7.91 (1H, d, J=8.1 Hz), 8.07 (1H, dd, J=2.5, 8.1 Hz), 8.27 (1H, d, J=2.5 Hz).

ESI (LC-MS positive mode) m/z 485 (M+H).

[α]$_D$:−50.4 (C=1.01, H$_2$O).

A compound of the formula (V) can readily be produced by the same procedure as any of those described in the above Examples or by any procedure of the above Examples to which a slight modification obvious to those skilled in the art is applied.

Formula (V)

Test Example 1

Measurement of Antitumor Effect

The antitumor effect of exemplary compounds of the present invention was measured.

The antitumor effect was determined using tumor-bearing mice prepared by subcutaneously implanting a human colon cancer cell line HCT116 obtained from American Type Culture Collection (Virginia, the United States of America) into flank of each BALB/c nude mouse purchased from Charles River, Japan. The purchased nude mice were quarantined for 1 week, and thereafter about 5×10$^6$ HCT116 cells were subcutaneously implanted into flank of each mouse. The mice were subjected to the experiment at the time when their tumor grew to a size of about 200 mm$^3$.

Each compound was dissolved in an administration solution, and the solution was administered to the tail vein at 0.1 mL per 10 g of body weight of each mouse. Administration was carried out twice in total; on the initiation day of administration and 7 days after the initiation day. The antitumor effect was calculated as tumor growth inhibition by comparing with tumor growth in the administration solution-administered control group 14 days after the initiation day of administration.

$$\text{Tumor growth inhibition } (TGI) = \left(1 - \frac{\text{mean tumor volume change in the treated group}}{\text{mean tumor volume change in the control group}}\right) \times 100(\%)$$

[Formula 12]

The results are shown in Table 1.

TABLE 1

| Test compound | Antitumor effect | |
| --- | --- | --- |
| | Dose (mg/kg) | TGI on day 14 (%) |
| Example 2 | 60 | 85 |
| Example 7 | 80 | 30 |

From the results of Test Example 1, it was confirmed that as to the stereochemistry of position 5 of an oxazolidinone ring, the S-form had higher antitumor effect than the R-form did, and a significant difference was recognized in effect between the S-form and the R-form.

Test Example 2

Measurement of Solubility

The solubility of exemplary compounds of the present invention was measured.

The measurement was carried out using an internal standard method, and a 4-point calibration curve (4000 μM, 1000 μM, 250 μM, and 31.3 μM, or 1000 μM, 250 μM, 62.5 μM, and 7.8 μM) was prepared. A sample solution (100% DMSO) was lyophilized, and each solution was added. Then, the mixture was stirred for 2 hours, and the sample dissolved in the solution was filtered. Thereafter, the filtrate was measured by HPLC (HPLC). Physiological saline was used as a solution. Note that among the test compounds used, comparative compound 1 was the compound of Example 3-26 described in International publication No. WO06/090743 (phosphoric acid dibenzyl ester(R)-2-oxo-3-[1-oxo-3-(2-trifluoromethylphenyl)-1,2-dihydroisoquinolin-7-yl]-oxazolidin-5-ylmethyl ester). Further, the optical isomer of comparative compound 1, i.e., phosphoric acid dibenzyl ester(S)-2-oxo-3-[1-oxo-3-(2-trifluoromethylphenyl)-1,2-dihydroisoquinolin-7-yl]-oxazolidin-5-ylmethyl ester, was used as comparative compound 2. An active substance of the compound of the present invention, i.e., 7-((S)-5-hydroxymethyl-2-oxooxazolidin-3-yl)-3-(2-trifluoromethylphenyl)-2H-isoquinolin-1-one, was used as comparative compound 3. Another active substance of the compound of the present invention, i.e., 7-((R)-5-hydroxymethyl-2-oxooxazolidin-3-yl)-3-(2-trifluoromethylphenyl)-2H-isoquinolin-1-one, was used as comparative compound 4. Structural formulas of comparative compounds 1, 2, 3, and 4 are shown in Table 2.

TABLE 2

Structural formula

Comparative compound 1

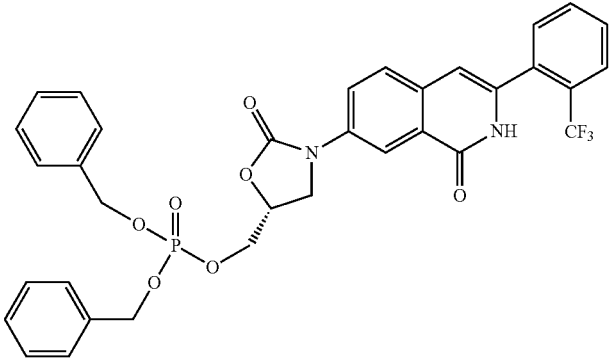 [SMILES: O=C1O[C@@H](COP(=O)(OCc2ccccc2)OCc2ccccc2)CN1c1ccc2cc(-c3ccccc3C(F)(F)F)[nH]c(=O)c2c1]

Comparative compound 2

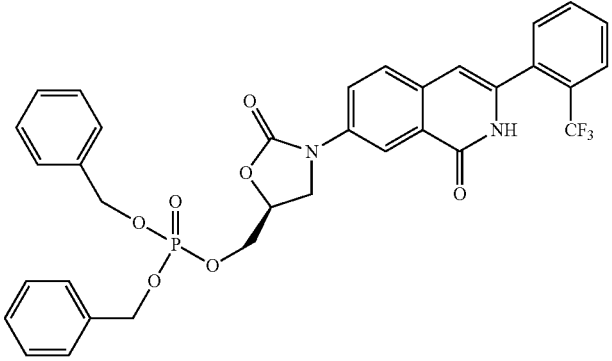 [SMILES: O=C1O[C@H](COP(=O)(OCc2ccccc2)OCc2ccccc2)CN1c1ccc2cc(-c3ccccc3C(F)(F)F)[nH]c(=O)c2c1]

TABLE 2-continued

Structural formula

Comparative compound 3

Comparative compound 4

The results are shown in Table 3. The compound of the present invention was excellent in water solubility, and showed adequate solubility in physiological saline, compared with comparative compounds 1, 2, 3, and 4.

TABLE 3

| Test compound | Solubility |
| --- | --- |
| Example 1 | 3530 μM |
| Example 2 | 3527 μM |
| Example 6 | >4000 μM |
| Example 7 | >4000 μM |
| Comparative compound 1 | <7.8 μM |
| Comparative compound 2 | <7.8 μM |
| Comparative compound 3 | 179 μM |
| Comparative compound 4 | 193 μM |

Test Example 3

Measurement of Conversion Rate in Human Plasma

The conversion rate of exemplary compounds of the present invention in human plasma was measured. The measurement of conversion rate in human plasma was conducted using human plasma purchased from Rockland Immunochemicals, Inc. (Pennsylvania, the United States of America). Each compound was incubated at 37° C. for 6 hours in plasma at a concentration of 50 μM, subjected to deproteinization treatment, and then quantified by HPLC using an internal standard method. The conversion rate was calculated as a residual rate after 6 hours. Comparative compounds 1 and 2 described above were also tested as test compounds. The results are shown in Table 4.

It was confirmed that the compound of the present invention had a half-life of not longer than 6 hours in human plasma, and that as the compound decreased, the active substance, 7-(5-hydroxymethyl-2-oxooxazolidin-3-yl)-3-(2-trifluoromethylphenyl)-2H-isoquinolin-1-one, was produced. On the contrary, almost all comparative compounds 1 and 2 remained in human plasma after 6 hours.

TABLE 4

| Test compound | Residual rate (after 6 hrs., %) |
| --- | --- |
| Example 1 | 35.4 |
| Example 2 | 29.4 |
| Example 7 | 33.4 |
| Comparative compound 1 | 99.5 |
| Comparative compound 2 | 95.5 |

The invention claimed is:

1. A compound of formula (I):

[Formula 1]

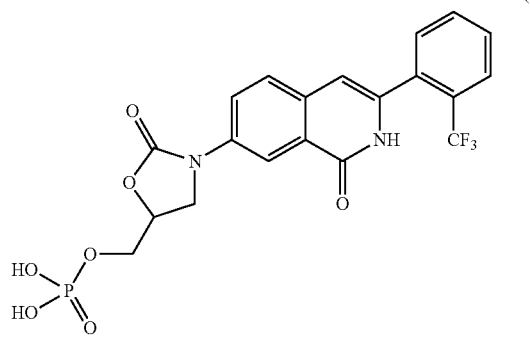

(I)

or a pharmaceutically acceptable salt thereof.

2. The compound of claim 1 in a form of a sodium or potassium salt.

3. The compound of claim 1 in a form of a disodium or monopotassium salt.

4. A crystal of a compound of formula (II):

[Formula 4]

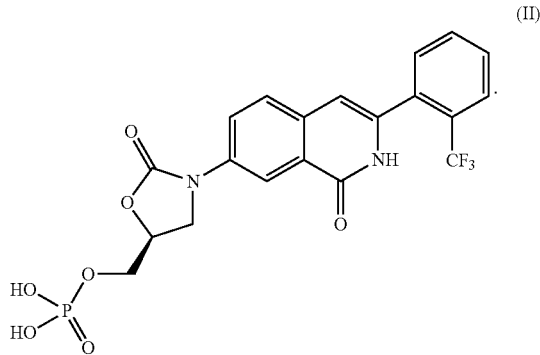

(II)

5. The crystal of the compound of formula (II) according to claim 4, wherein the crystal has peaks at diffraction angles (2θ) of around 3.9°, 9.1°, 10.7°, 13.4°, 18.0°, 21.6°, 23.8°, and 24.8° in powder X-ray diffraction.

6. The crystal of the compound of formula (II) according to claim 4, wherein the crystal has peaks at diffraction angles (2θ) of around 3.3°, 3.9°, 9.1°, 10.7°, 11.9°, 13.4°, 14.2°, 15.2°, 16.5°, 17.4°, 18.0°, 19.2°, 19.9°, 20.6°, 21.6°, 22.1°, 22.6°, 23.8°, 24.3°, 24.8°, and 25.6° in powder X-ray diffraction.

7. A crystal of a monopotassium salt of a compound of formula (II):

[Formula 5]

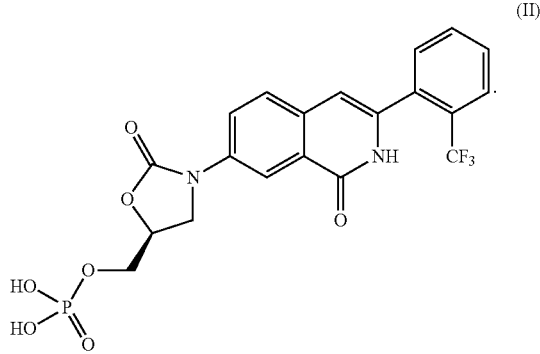

(II)

8. The crystal of the monopotassium salt of the compound of formula (II) according to claim 7, wherein the crystal has peaks at diffraction angles (2θ) of around 4.5°, 9.2°, 12.2°, 16.6°, 18.7°, 21.2°, 22.4°, and 26.2° in powder X-ray diffraction.

9. The crystal of the monopotassium salt of the compound of formula (II) according to claim 7, wherein the crystal has peaks at diffraction angles (2θ) of around 3.6°, 4.5°, 9.2°, 10.9°, 12.2°, 13.7°, 15.3°, 16.6°, 18.0°, 18.7°, 19.3°, 21.2°, 22.4°, 24.3°, 26.2°, and 28.8° in powder X-ray diffraction.

10. A pharmaceutical composition comprising the compound of claim 1, or a pharmaceutically acceptable salt as an active ingredient.

11. The pharmaceutical composition of claim 10, wherein a dosage form of the composition is an injection.

12. A pharmaceutical composition comprising the crystal of claim 4 as an active ingredient.

13. A pharmaceutical composition comprising the crystal of claim 7 as an active ingredient.

14. A method for treating a malignant tumor, comprising administering to a patient in need thereof the pharmaceutical composition of claim 10.

15. The method of claim 14, wherein the malignant tumor is a solid cancer.

16. A method for treating a malignant tumor, comprising administering to a patient in need thereof the pharmaceutical composition of claim 12.

17. The method of claim 16, wherein the malignant tumor is a solid cancer.

18. A method for treating a malignant tumor, comprising administering to a patient in need thereof the pharmaceutical composition of claim 13.

19. The method of claim 18, wherein the malignant tumor is a solid cancer.

* * * * *